Figure 1:
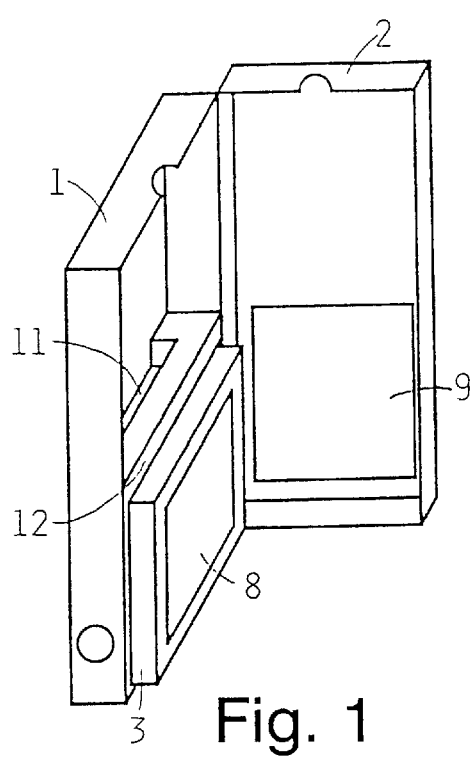

United States Patent
Poulsen et al.

[19]

[11] Patent Number: 5,984,894
[45] Date of Patent: Nov. 16, 1999

[54] INFUSER

[75] Inventors: Jens Ulrik Poulsen, Copenhagen; Thomas Munk Plum, Skodsborg; Jens Moller-Jensen, Copenhagen, all of Denmark

[73] Assignee: Novo Nordisk A/S, Bagsvaerd, Denmark

[21] Appl. No.: 08/858,941

[22] Filed: May 20, 1997

Related U.S. Application Data

[63] Continuation-in-part of application No. 08/321,665, Oct. 12, 1994, abandoned, which is a continuation of application No. 08/122,436, Sep. 24, 1993, abandoned.

[30] Foreign Application Priority Data

Apr. 18, 1991 [DK] Denmark ................................. 694/91

[51] Int. Cl.[6] .................................................. A61M 5/00
[52] U.S. Cl. .............................. 604/151; 604/67; 604/260
[58] Field of Search .............................. 604/65, 67, 132, 604/142, 151, 153, 262, 404, 410, 255, 259, 260; 222/325, 333, 383.1

[56] References Cited

U.S. PATENT DOCUMENTS

| | | |
|---|---|---|
| 4,395,259 | 7/1983 | Prestele et al. . |
| 4,468,221 | 8/1984 | Mayfield . |
| 4,624,661 | 11/1986 | Arimond . |
| 4,643,279 | 2/1987 | Samiotes et al. . |
| 4,685,903 | 8/1987 | Cable et al. . |
| 5,181,910 | 1/1993 | Scanton . |
| 5,256,157 | 10/1993 | Samiotes et al. . |

FOREIGN PATENT DOCUMENTS

| | | |
|---|---|---|
| 0 062 974 | 10/1982 | European Pat. Off. . |
| 0 275 213 | 7/1988 | European Pat. Off. . |
| 0 399 119 | 11/1990 | European Pat. Off. . |
| WO 85/00523 | 2/1985 | WIPO . |

*Primary Examiner*—Wynn Wood Coggins
*Assistant Examiner*—A. T. Nguyen
*Attorney, Agent, or Firm*—Steve T. Zelson, Esq.

[57] ABSTRACT

An infuser for infusing a liquid from a reservoir, comprising a durable part (1,2,3) forming a housing and a disposable part (4) containing the liquid reservoir and an energy reservoir for energizing the pumping function. The infuser, further, contains in its disposable part (4) all liquid-contacting elements of the device, and the disposable part (4) and the durable part (1,2,3) are provided with mating coupling means (10,11).

A controlling unit in an electronic compartment (3) of the durable part (1,2,3) has a socket (12) into which a plug (13) may be inserted, the plug (13) contains a ROM carrying information defining infusion data. The plug (13) has a transparent sheet (14) covering a display (8) of the durable part when the plug (13) is inserted in the socket (12). The sheet (14) carries a graphic representation of the information in the ROM to be seen in relation to information displayed on the display (8).

17 Claims, 2 Drawing Sheets

INFUSER

CROSS-REFERENCE TO RELATED APPLICATIONS

This application is a continuation-in-part of application Ser. No. 08/321,665 filed Oct. 12, 1994, now abandoned, which is a continuation of Ser. No. 08/122,436 filed Sep. 24, 1993, now abandoned, and claims priority under 35 U.S.C. 119 of Danish application serial no. 694/91 filed Apr. 18, 1991, the contents of which are fully incorporated herein by reference.

The invention relates to pumps for current infusion of liquid, preferably insulin.

By insulin treatment of type 1 diabetes a syringe, a pen, or a pump are used.

The pump offers the possibility of a good controlling of the glucose concentration as it may simulate the course of the insulin production by a non-diabetic. However, the use of insulin pumps has been rather limited as pump treatment has been looked on as a strict treatment and as the pumps have been complex to operate.

Consequently, the basis for the invention is the wish of making it clear that an insulin pump allows a free life style with a good control of the glucose and may be very simple to use.

The object of the invention is to provide an insulin pump which may be worn without dislike and which is extremely simple to operate.

This is obtained by a pump according to claim 1. By integrating more disposable parts in a single unit the apparatus is made more simple to handle than known apparatus wherein a cartridge, an infusion line, and batteries for the pumping motor must be changed individually.

From WO 85/00523 it is known to integrate the power source for the pump into a disposable part which further comprises an infusion line for insertion into a pump head to provide a peristaltic pump. This insertion complicates the mounting of the disposable part.

Such complications are overcome as according to this invention all liquid contacting parts of the pumping mechanism and of possible sensors measuring the pressure in the catheter directly in the outlet from the pumping mechanism are integrated in a unit to be mounted concomitantly to the durable part by a single operation bringing into engagement mating coupling elements on the durable part and on the disposable part.

The means for setting the controlling unit may comprise a socket with electric contacts, which socket is designed to receive and communicate with a plug having corresponding electric contacts and carrying a programmed ROM-circuit defining the infusion data. The plug may further carry a graphic representation of the infusion data stored in the ROM, i.e. how the infusion of a set 24-hours' dose is distributed over the 24 hours. This graphic representation may be marks on a transparent sheet so secured to the plug that it covers a watch dial display when the plug is inserted in the socket, the marks indicating periods with increased or decreased infusion. By this construction the user may avoid the relatively complicated programming of the pump as he may plan the needed infusion profile or profiles in cooperation with his medical adviser and thereafter he will only have to insert the plug which is in accordance with his immediate life style.

The disposable part may further comprise a memory keeping an account of the amount of liquid left in the reservoir. By enclosing such a memory in the disposable part containing the liquid reservoir, this memory is firmly connected to the reservoir. This is appropriate if the memory shall be able to keep an account of the amount of liquid left in the reservoir. Data in the memory may be read out by the control unit and represented on the display.

According to the invention the durable part may comprise one or more of the elements: A controlling unit, a display, means for setting the controlling unit, a drive unit delivering mechanical energy for driving the pump mechanism and a long life electric cell energizing the controlling unit. The pumping mechanism may be a complete low cost pump, e.g. a piezoelectric membrane pump, which may be disposed of after use. In other embodiments the pump mechanism is only the part comprising a pumping chamber and valves, and this mechanism is driven by an electric motor which is integrated in the durable part. When the controlling unit is energized by its own electric cell it is avoided that data stored in this unit are deleted during the change of the disposable part. It is possible to energize the controlling unit from the energy reservoir in the disposable part so that only during change the energizing is switched over to the long life cell in the durable part whereby this cell only acts as an emergency power supply.

To establish the necessary communication between the durable and the disposable part, these parts are provided with cooperating sets of electric contacts and cooperating coupling parts so that electrical and mechanical connections are established concomitantly when the disposable part is mounted to the durable part.

The mounting may easily be made when the durable and the disposable parts in a complementary way fill the inner space of the housing whereby the disposable part is unambiguously secured in the housing.

As a result no problems exist whether the cartridge is correctly inserted, the infusion line is correctly coupled to the pump, or the batteries could be used for the infusion of the content of one cartridge more. All that should be done is to place a new disposable part in the housing and close this housing.

Figure 2:
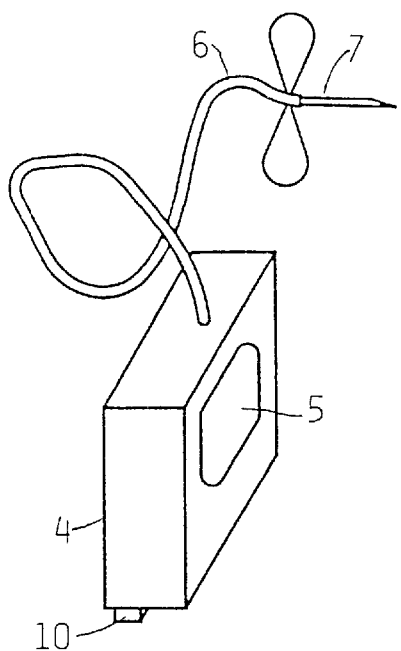
Figure 3:
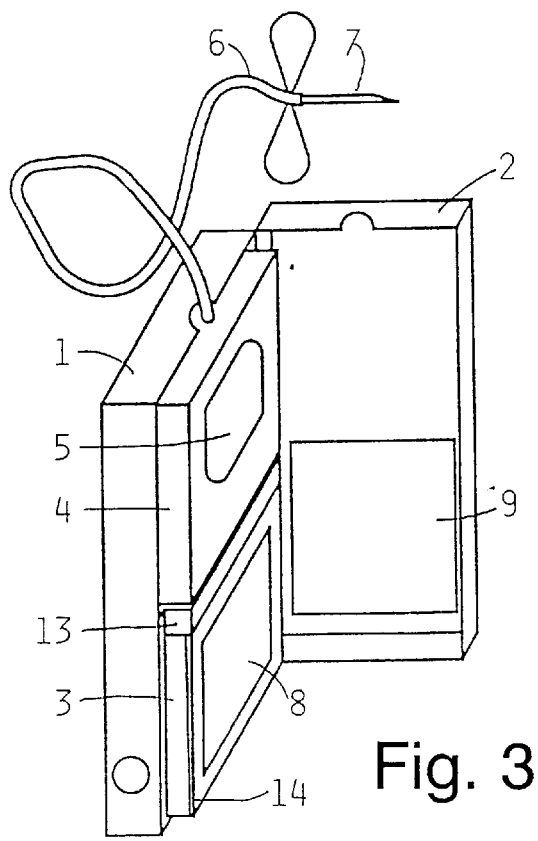
Figure 4:
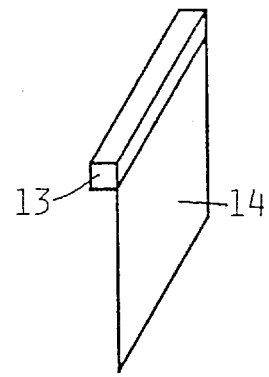
Figure 5:
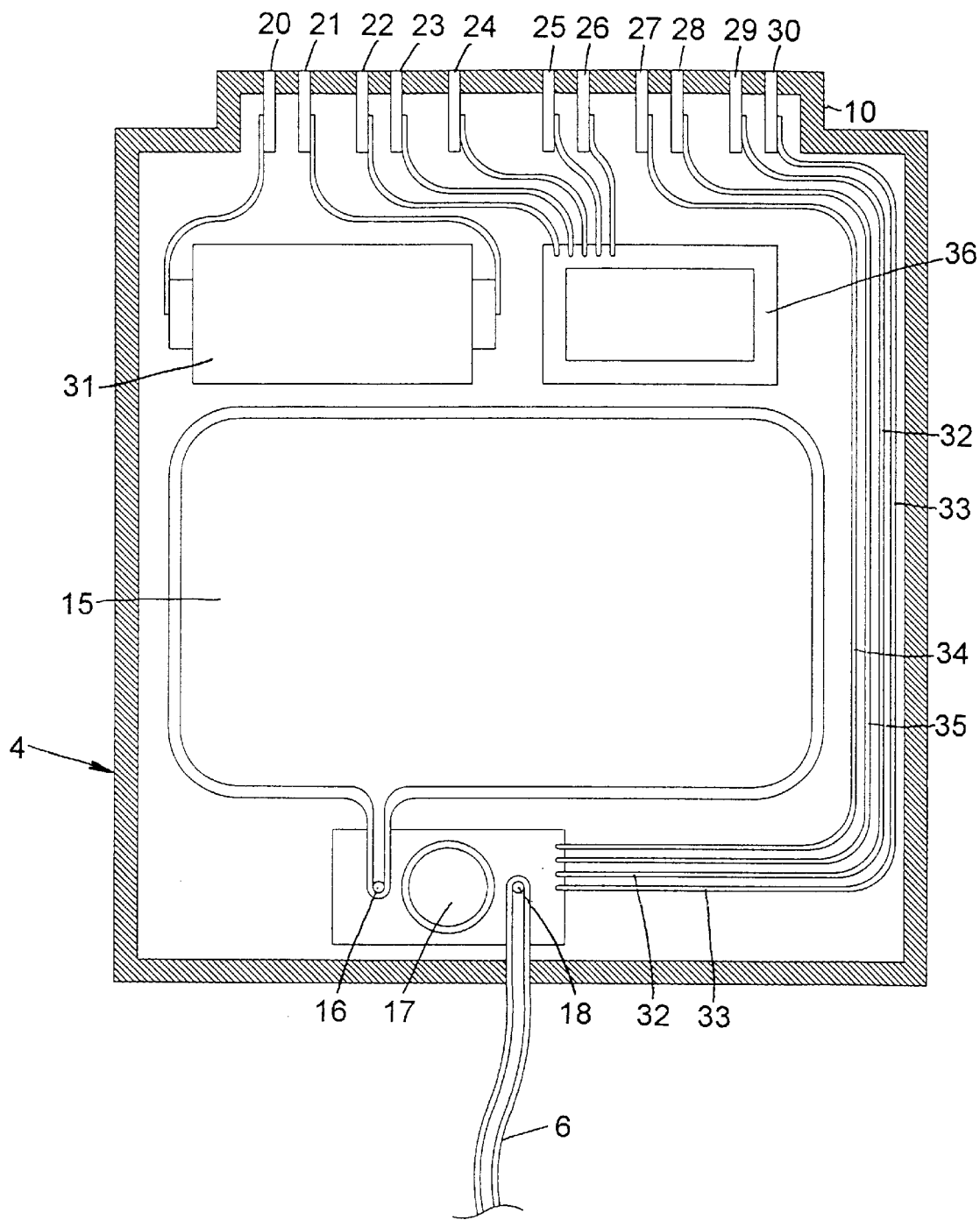

The invention will now be explained in further details with reference to the drawing, in which FIG. 1 shows the durable part of a pump according to the invention, FIG. 2 shows the disposable part of a pump according to the invention, FIG. 3 shows the disposable part of FIG. 2 mounted in the durable part, which is shown with its lid open, FIG. 4 shows an infusion data carrying plug with an attached information sheet, and FIG. 5 shows schematically the components comprised by the disposable part of a pump according to the invention.

The infusion apparatus shown in FIG. 1 has a durable part forming a housing and comprising a bottom part 1 and a lid 2 hinged to this bottom part. In one end of the bottom part 1 there is an electronic compartment 3 comprising a controlling unit and a display 8.

In the other end of the bottom part 1 space is left for receiving a disposable part 4 as shown in FIG. 2. This disposable part contains an insulin reservoir made inspectable through a window 5. The disposable part further contains a pump mechanism for delivering the insulin through an infusion line 6 to a needle 7 for insertion in the tissue of the patient.

The energy for the pump is supplied by a battery in the disposable part. This battery is designed with a capacity sufficient to energize the pump during the emptying of the insulin reservoir.

In a preferred embodiment, the disposable part comprises a sensor placed at the inlet of the infusion line and designed to be coupled to a measuring device.

As it appears, all parts which have to be changed frequently are integrated in the disposable part. The time for changing is defined by the draining of the insulin reservoir and it is automatically ensured that also the battery and the infusion line are changed.

In this preferred embodiment, also members which are not normally changed so as the pump mechanism and the sensor are integrated in the disposable part.

FIG. 3 shows a pump with the disposable part mounted in the bottom part. By this mounting sets of electrical contacts contained in a plug 10 and socket 11, in the disposal and the durable part, respectively, establish electrical connections between the disposable part 4 and the durable part 3 which controls the infusion.

FIG. 5 shows schematically a disposable part 4 comprising an insulin reservoir 15 which through a tubing is connected to an inlet 16 to an electronic micro pump 17 which in a controlled way delivers insulin through an outlet 18 to which a infusion line 6 is connected.

Along one of its sides the housing of the disposable part has an oblong plug 10 carrying a number of electric contacts 20–30 which are connected to corresponding not shown contacts in a socket 11 mating to said plug 10 on the durable part.

The disposable part contains a battery 31 having a capacity enabling it to energize the whole device for the injection of the content of the reservoir, i. e. to deliver the energy necessary for the mechanical pumping work and for the energizing of the control circuit during the time it takes to empty the reservoir by normal use of the device, e.g for a week. The battery is connected to the contacts 20 and 21 in the plug 10 of the disposable part from where electric power is delivered to the durable part. The controlling circuit in this durable part controls the electric energy fed to the micro pump through the contacts 29 and 30 and electric leads 32 and 33 in the disposable part.

In connection with the outlet 18 of the micro pump a not shown sensor monitoring the pressure in the infusion line is mounted. By currently monitoring of the pressure in the outlet infusion line from a volumetric pump an estimate of the operation conditions of the whole device may be obtained as described in U.S. Pat. No. 5,190,522. Measuring signals from the sensor is through electric leads 34 and 35 led to the contacts 27 and 28 and there through to the durable part in which the signals are evaluated.

Further the disposable part comprises a memory 36. This may be an electronic memory wherein a number corresponding to the number of units of medicine in the reservoir is stored. The content of the memory may be read by the electronic circuit in the durable part which circuit may also write into the memory. Reading and writing is established through leads which through the contacts 22 to 26 are connected to the durable part. When the disposable part is new and not used the memory 36 is by the manufacturer set to a number corresponding to the number of units of medicine stored in the insulin reservoir. Each time the controlling circuit in the durable part controls the micro pump to deliver one unit of medicine through the catheter a subtraction by one is made in the memory 36. This way the memory will keep account of the number of units of medicine left in the reservoir and store this number when the disposable part is removed from the durable part before the reservoir is empty, e. g if the user want to change temporarily to another type of insulin.

When the disposable part is mounted in the bottom part 1 of the housing, the lid 2 is closed and is kept closed by a locking mechanism. The lid 2 is provided with a window 9 which reveals the relevant part of the display when the lid 2 is closed.

In FIG. 1 another set of not visible electric contacts are provided in a socket 12 mating a linear plug 13 as shown in FIG. 3. The contacts of the plug 13 are connected to a ROM circuit in said plug, in which ROM circuit a program for the control circuit is stored which program defines how a set 24-hours' dose should be distributed taking into account that the need for insulin varies during a day and a night depending on the patient's life style. This feature makes it easy for the patient to change the 24 hours' infusion profile in accordance with changes in life style, e.g. from working days to week-ends or holidays, just by inserting another plug 13 into the socket whereby the programming of the control circuit is changed to the program stored in the ROM in the inserted plug 13.

FIG. 4 shows such a plug 13 being provided with a transparent sheet which is attached to the plug 13 so that it covers the display 8 of the durable part of the pump when the plug 13 is inserted into the socket 12 of this durable part. The sheet 14 may carry information of the infusion profile obtained with the current plug. The sheet being transparent the information may be a graphic indication of periods in which the insulin infusion rate is higher or lower than the average which indication may be seen in connection with information shown on the display 8.

The apparatus is described as a pump for infusing insulin, but may be used for other kinds of timed medication without deviating from the scope of the invention.

Further the reservoir may be a well known ampoule from which medicine is pressed out by a piston which is pressed into the ampoule. The piston may be operated by a piston rod which together with the piston forms the pumping device. The advancing of the piston rod may be obtained by energising a motor in the durable part from the battery in the disposable part. The memory in the disposable part may be the mechanical memory obtained due to the fact that the position of the piston in the ampoule is at any time indicated the size of the volume left in the ampoule.

We claim:

1. An infusion system comprising:
   a housing for receiving a replaceable unit; and
   a self-contained, replaceable unit having: a reservoir containing a liquid to be infused, an infusion line communicating with said reservoir, a pump for pumping liquid from said reservoir out through said infusion line, an energy reservoir for operating said pump, and a memory for storing a value representing the amount of liquid remaining in said reservoir; and
   wherein said housing and replaceable unit further include a mating coupling for releasably securing said replaceable unit within said housing so as to allow said replaceable unit to be readily removed and replaced when desired, and wherein a portion of said infusion line extends to the exterior of said housing.

2. The infusion system according to claim 1, wherein said replaceable unit further comprises a sensor for continuously measuring the pressure in said infusion line.

3. The infusion system according to claim 1, further comprising a control unit mounted in said housing with a means for setting said control unit, and a long life electrical cell for maintaining the settings of said control unit; and wherein said mating coupling couples said control unit to said pump for controlling the operation of said pump.

4. The infusion system according to claim 3, further comprising a display connected to said control unit and mounted in said housing so as to be visible from outside said housing.

5. The infusion system according to claim 3, wherein said mating coupling includes electrical contacts for connecting said energy source to said control unit, electrical contacts for connecting said control unit to said pump for providing power from said energy source to said pump, and electrical contacts for connecting said control unit to said memory.

6. The infusion system according to claim 5, wherein said housing includes a socket for receiving a plug-in unit, wherein said socket has electrical contacts communicating with said control unit, and further comprising a plug-in unit having information for defining infusion rates and electrical contacts cooperating with the electrical contacts of said socket for transmitting such information to said control unit.

7. The infusion system according to claim 5, wherein said replaceable unit further comprises a sensor for continuously measuring the pressure in said infusion line, and wherein said mating coupling includes electrical contacts for connecting said sensor to said control unit.

8. The infusion system according to claim 7, wherein said housing includes a socket for receiving a plug-in unit, wherein said socket has electrical contacts communicating with said control unit, and further comprising a plug-in unit having information for defining infusion rates and electrical contacts cooperating with the electrical contacts of said socket for transmitting such information to said control unit.

9. The infusion system according to claim 3, wherein said housing includes a socket for receiving a plug-in unit, wherein said socket has electrical contacts communicating with said control unit, and further comprising a plug-in unit having information for defining infusion rates and electrical contacts cooperating with the electrical contacts of said socket for transmitting such information to said control unit.

10. The infusion system according to claim 9, wherein said plug-in unit further includes an exterior, visual representation of the infusion rate information contained therein.

11. The infusion system according to claim 10, further comprising a display connected to said control unit and mounted in said housing so as to be visible from outside said housing, wherein said plug-in unit includes a transparent sheet, wherein said visual representation is contained on said transparent sheet, and wherein said sheet is positioned so that, when said plug-in unit is mounted in said socket, said sheet overlies said display so as to be visible from outside said housing.

12. The infusion system according to claim 1, comprising at least one control member mounted in said housing for controlling the operation of said pump, and wherein said mating coupling includes cooperating electrical contacts to establish an electrical connection between said pump and said control member.

13. The infusion system according to claim 12, wherein said replaceable unit is a complement to said housing so as to fill the space of said housing, whereby the replaceable unit is unambiguously secured in said housing.

14. The infusion system according to claim 1, wherein said mating coupling includes a plug secured relative to one of said housing and said replaceable unit and a mating socket secured relative to the other of said housing and said replaceable unit for releasably securing said replaceable unit against movement in said housing.

15. A self-contained, replacement unit for use in an infusion system having a housing and at least one control member, said replacement unit comprising: a reservoir containing a liquid to be infused, an infusion line communicating with said reservoir, a pump for pumping liquid from said reservoir out through said infusion line, an energy reservoir for operating said pump, a memory for storing a value representing the amount of liquid remaining in said reservoir and a coupling which includes electrical contacts connected to pump and memory which can engage a cooperating coupling in a housing of an infusion system having a control member, for releasably securing said replacement unit within said housing and providing electrical communication between said pump and memory and the control member.

16. The replacement unit according to claim 15, further comprising a sensor for continuously measuring the pressure in said infusion line.

17. The replacement unit according to claim 15, wherein said coupling includes an electrical contact connected to said energy reservoir such that, when said coupling engages a cooperating coupling in a housing of an infusion system having a control member, said energy reservoir is connected to the control member.

\* \* \* \* \*